US007927838B2

United States Patent
Shannon

(10) Patent No.: US 7,927,838 B2
(45) Date of Patent: *Apr. 19, 2011

(54) METHOD FOR LINEAR MRNA AMPLIFICATION

(75) Inventor: Karen W. Shannon, Los Gatos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1161 days.

This patent is subject to a terminal disclaimer.

(21) Appl. No.: 11/179,813

(22) Filed: Jul. 11, 2005

(65) Prior Publication Data

US 2006/0024799 A1    Feb. 2, 2006

Related U.S. Application Data

(63) Continuation of application No. 09/690,173, filed on Oct. 16, 2000, now Pat. No. 6,916,633, which is a continuation of application No. 09/322,692, filed on May 28, 1999, now Pat. No. 6,132,997.

(51) Int. Cl.
*C12Q 1/68* (2006.01)
*C12P 19/34* (2006.01)
*C07H 21/04* (2006.01)

(52) U.S. Cl. ......... 435/91.2; 435/6; 435/91.1; 536/24.3; 536/24.1

(58) Field of Classification Search .................. None
See application file for complete search history.

(56) References Cited

U.S. PATENT DOCUMENTS

| | | | |
|---|---|---|---|
| 4,683,195 A | 7/1987 | Mullis et al. | |
| 5,130,238 A | 7/1992 | Malek et al. | |
| 5,399,491 A | 3/1995 | Kacian et al. | |
| 5,437,990 A | 8/1995 | Burg et al. | |
| 5,514,545 A | 5/1996 | Eberwine | |
| 5,545,522 A | 8/1996 | Van Gelder et al. | |
| 5,554,516 A | 9/1996 | Kacian et al. | |
| 5,693,502 A * | 12/1997 | Gold et al. ................ | 435/91.2 |
| 5,716,785 A | 2/1998 | Van Gelder et al. | |
| 5,932,451 A | 8/1999 | Wang et al. | |
| 6,132,997 A | 10/2000 | Shannon | |

FOREIGN PATENT DOCUMENTS

WO    WO 91/06554    5/1991

OTHER PUBLICATIONS

Eberwine et al. "Amplification of mRNA Populations using aRNA Generatied from Immobilized Oligo (dt)-T7 Primed cDNA," Biotechniques (1996) 20:584-591.
Eberwine et al. "Complementary DNA Synthesis In Situ: Methods and Application," Methods in Enzymology (1992) 216:80-100.
Eberwine et al. "Analysis of Gene Expression in Single Live Neurons," Proc. Natl Acad Sci. USA (1992) 89:3010-3014.
Phillips et al. "Antisense RNA Amplification: A Linear Amplification Method for Analyzing the mRNA Population from Single Living Cells," Methods (1996) 10:283-288.

* cited by examiner

*Primary Examiner* — Janet L Epps-Smith

(57) ABSTRACT

Methods for linearly amplifying mRNA to produce antisense RNA are provided. In the subject methods, mRNA is converted to double-stranded cDNA using a promoter-primer having a poly-dT primer site linked to a promoter sequence so that the resulting double-stranded cDNA is recognized by an RNA polymerase. The resultant double-stranded cDNA is then transcribed into antisense RNA in the presence of a reverse transcriptase that is rendered incapable of RNA-dependent DNA polymerase activity during this transcription step. The subject methods find use a variety of different applications in which the preparation of linearly amplified amounts of antisense RNA is desired. Also provided are kits for practicing the subject methods.

28 Claims, 1 Drawing Sheet

SEQUENCE LISTING

<160> NUMBER OF SEQ ID NOS: 1

<210> SEQ ID NO 1
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 46
<223> OTHER INFORMATION: N=A, G, C, or T

<400> SEQUENCE: 1
aattaatacg actcactata gggagatttt tttttttttt ttttvn     46

US 7,927,838 B2

METHOD FOR LINEAR MRNA AMPLIFICATION

CROSS REFERENCE TO RELATED APPLICATIONS

This application is a continuation of U.S. patent application Ser. No. 09/690,173, filed Oct. 16, 2000 now U.S. Pat. No. 6,916,633, which is a continuation of U.S. patent application Ser. No. 09/322,692, filed May 28, 1999, now issued U.S. Pat. No. 6,132,997 from which priority is claimed under 35 U.S.C. 120. The entireties of these applications are incorporated herein by reference.

INTRODUCTION

1. Technical Field

The technical field of this invention is the enzymatic amplification of nucleic acids.

2. Background of the Invention

The characterization of cellular gene expression finds application in a variety of disciplines, such as in the analysis of differential expression between different tissue types, different stages of cellular growth or between normal and diseased states. Fundamental to differential expression analysis is the detection of different mRNA species in a test population, and the quantitative determination of different mRNA levels in that test population. However, the detection of rare mRNA species is often complicated by one or more of the following factors: cell heterogeneity, paucity of material, or the limits of detection of the assay method. Thus, methods which amplify heterogeneous populations of mRNA that do not introduce significant changes in the relative amounts of different mRNA species facilitate this technology.

A number of methods for the amplification of nucleic acids have been described. Such methods include the "polymerase chain reaction" (PCR) (Mullis et al., U.S. Pat. No. 4,683,195), and a number of transcription-based amplification methods (Malek et al., U.S. Pat. No. 5,130,238; Kacian and Fultz, U.S. Pat. No. 5,399,491; Burg et al., U.S. Pat. No. 5,437,990). Each of these methods uses primer-dependent nucleic acid synthesis to generate a DNA or RNA product, which serves as a template for subsequent rounds of primer-dependent nucleic acid synthesis. Each process uses (at least) two primer sequences complementary to different strands of a desired nucleic acid sequence and results in an exponential increase in the number of copies of the target sequence. These amplification methods can provide enormous amplification (up to billion-fold). However, these methods have limitations which make them not amenable for gene expression monitoring applications. First, each process results in the specific amplification of only the sequences that are bounded by the primer binding sites. Second, exponential amplification can introduce significant changes in the relative amounts of specific target species—small differences in the yields of specific products (for example, due to differences in primer binding efficiencies or enzyme processivity) become amplified with every subsequent round of synthesis.

Amplification methods that utilize a single primer are amenable to the amplification of heterogeneous mRNA populations. The vast majority of mRNAs carry a homopolymer of 20-250 adenosine residues on their 3' ends (the poly-A tail), and the use of poly-dT primers for cDNA synthesis is a fundamental tool of molecular biology. "Single-primer amplification" protocols have been reported (see e.g. Kacian et al., U.S. Pat. No. 5,554,516; Van Gelder et al., U.S. Pat. No. 5,716,785). The methods reported in these patents utilize a single primer containing an RNA polymerase promoter sequence and a sequence complementary to the 3'-end of the desired nucleic acid target sequence(s) ("promoter-primer"). In both methods, the promoter-primer is added under conditions where it hybridizes to the target sequence(s) and is converted to a substrate for RNA polymerase. In both methods, the substrate intermediate is recognized by RNA polymerase, which produces multiple copies of RNA complementary to the target sequence(s) ("antisense RNA"). Each method uses, or could be adapted to use, a primer containing poly-dT for amplification of heterogeneous mRNA populations.

Amplification methods that proceed linearly during the course of the amplification reaction are less likely to introduce bias in the relative levels of different mRNAs than those that proceed exponentially. In the method described in U.S. Pat. No. 5,554,516, the amplification reaction contains a nucleic acid target sequence, a promoter-primer, an RNA polymerase, a reverse transcriptase, and reagent and buffer conditions sufficient to allow amplification. The amplification proceeds in a single tube under conditions of constant temperature and ionic strength. Under these conditions, the antisense RNA products of the reaction can serve as substrates for further amplification by non-specific priming and extension by the RNA-dependent DNA polymerase activity of reverse transcriptase. As such, the amplification described in U.S. Pat. No. 5,554,516 proceeds exponentially. In contrast, in specific examples described in U.S. Pat. No. 5,716,785, cDNA synthesis and transcription occur in separation reactions separated by phenol/chloroform extraction and ethanol precipitation (or dialysis), which may incidentally allow for the amplification to proceed linearly since the RNA products cannot serve as substrates for further amplification.

The method described in U.S. Pat. No. 5,716,785 has been used to amplify cellular mRNA for gene expression monitoring (for example, R. N. Van Gelder et al. (1990), Proc. Natl. Acad. Sci. USA 87, 1663; D. J. Lockhart et al. (1996), Nature Biotechnol. 14, 1675). However, this procedure is not readily amenable to high throughput processing. In preferred embodiments of the method described in U.S. Pat. No. 5,716,785, poly-A mRNA is primed with a promoter-primer containing poly-dT and converted into double-stranded cDNA using a method described by Gubler and Hoffman (U. Gubler and B. J. Hoffman (1983), Gene 25, 263-269) and popularized by commercially available kits for cDNA synthesis. Using this method for cDNA synthesis, first strand synthesis is performed using reverse transcriptase and second strand cDNA is synthesized using RNaseH and DNA polymerase I. After phenol/chloroform extraction and dialysis, double-stranded cDNA is transcribed by RNA polymerase to yield antisense RNA product. The phenol/chloroform extractions and buffer exchanges required in this procedure are labor intensive, and are not readily amenable to robotic handling.

Accordingly, there is interest in the development of improved methods of antisense RNA amplification. Of particular interest would be the development of a linear amplification protocol that did not require a reverse transcriptase separation step.

RELEVANT LITERATURE

United States Patents disclosing methods of antisense RNA synthesis include: U.S. Pat. Nos. 5,716,785; 5,554,516; 5,545,522; 5,437,990; 5,130,238; and 5,514,545. Antisense RNA synthesis is also discussed in Phillips and Eberwine (1996), Methods: A companion to Methods in Enzymol. 10, 283; Eberwine et al. (1992), Proc., Natl., Acad. Sci. USA 89, 3010; Eberwine (1996), Biotechniques 20, 584; and Eberwine et al. (1992), Methods in Enzymol. 216, 80.

SUMMARY OF THE INVENTION

Methods for linearly amplifying mRNA to produce RNA (particularly as antisense RNA) are provided. In the subject methods, mRNA is converted to cDNA (particularly double-stranded cDNA) using a promoter-primer particularly having a poly-dT primer site linked to a promoter sequence so that the resulting cDNA is recognized by an RNA polymerase. The resultant cDNA is then transcribed into RNA (particularly antisense RNA) in the presence of a reverse transcriptase that is rendered incapable of RNA-dependent DNA polymerase activity during this transcription step. The subject methods find use a variety of different applications in which the preparation of linearly amplified amounts of antisense RNA is desired. Also provided are kits for practicing the subject methods.

DESCRIPTION OF THE SPECIFIC EMBODIMENTS

Figure 1:
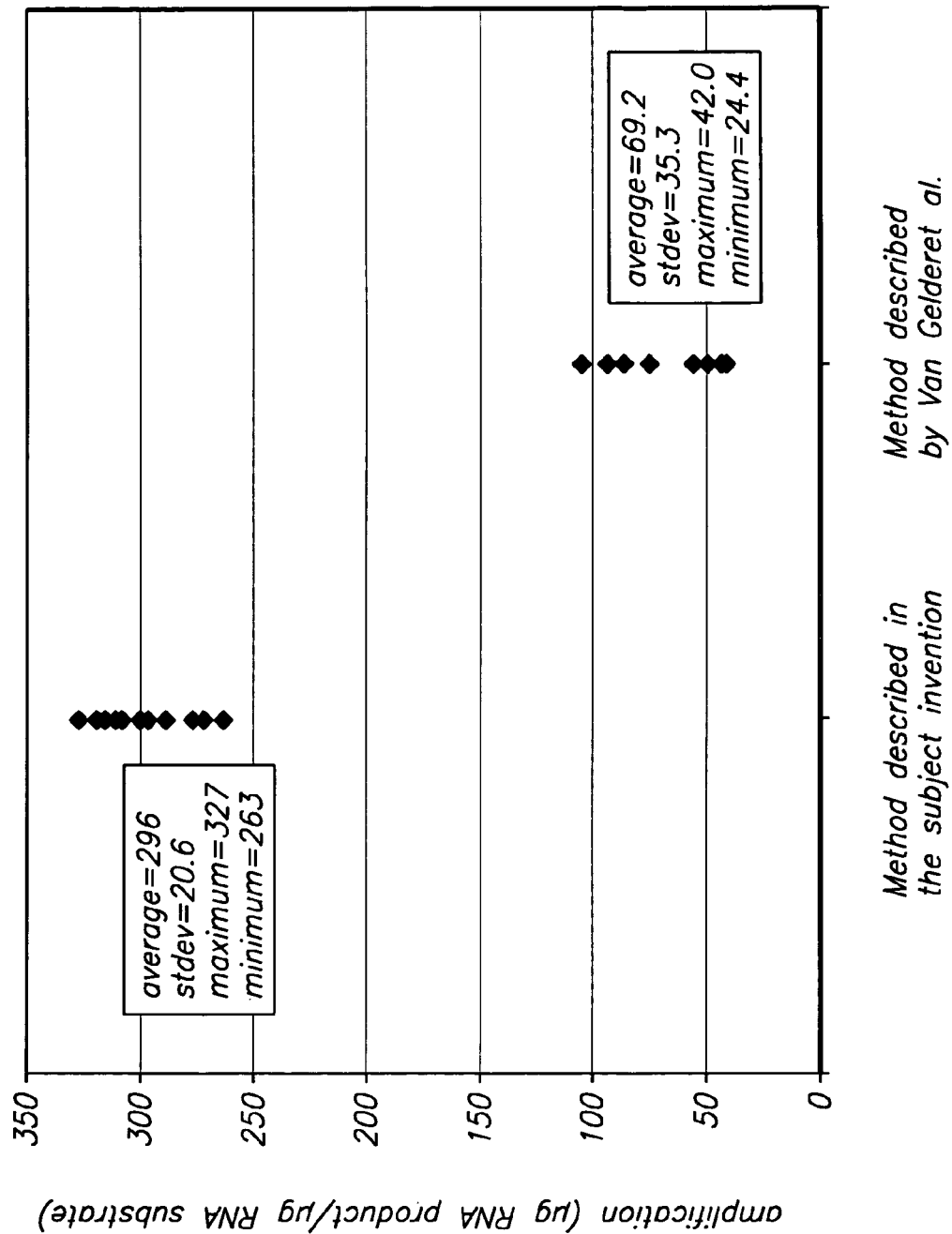
FIG. 1 provides a graphical representation of the results obtained using the subject methods versus those described in U.S. Pat. No. 5,716,785.

Methods for linearly amplifying mRNA to produce antisense RNA are provided. In the subject methods, mRNA is converted to double-stranded cDNA using a promoter-primer having a poly-dT primer site linked to a promoter sequence so that the resulting double-stranded cDNA is recognized by an RNA polymerase. The resultant double-stranded cDNA is then transcribed into antisense RNA in the presence of a reverse transcriptase that is rendered incapable of RNA-dependent DNA polymerase activity during this transcription step. The subject methods find use in a variety of different applications in which the preparation of linearly amplified amounts of antisense RNA is desired. Also provided are kits for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a", "an" and "the" include plural reference unless the context clearly dictates otherwise. Unless defined otherwise all technical and scientific terms used herein have the same meaning as commonly understood to one of ordinary skill in the art to which this invention belongs.

The subject invention provides methods for linearly amplifying mRNA into antisense RNA. As such, the subject invention provides methods of producing amplified amounts of antisense RNA from an initial amount of mRNA. By amplified amounts is meant that for each initial mRNA, multiple corresponding antisense RNAs, where the term antisense RNA is defined here as ribonucleic acid complementary to the initial mRNA, are produced. By corresponding is meant that the antisense RNA shares a substantial amount of sequence identity with the sequence complementary to the mRNA (i.e. the complement of the initial mRNA), where substantial amount means at least 95% usually at least 98% and more usually at least 99%, where sequence identity is determined using the BLAST algorithm, as described in Altschul et al. (1990), J. Mol. Biol. 215:403-410 (using the published default setting, i.e. parameters w=4, t=17). Generally, the number of corresponding antisense RNA molecules produced for each initial mRNA during the subject linear amplification methods will be at least about 10, usually at least about 50 and more usually at least about 100, where the number may be as great as 600 or greater, but often does not exceed about 1000.

In the first step of the subject methods, an initial mRNA sample is subjected to a series of enzymatic reactions under conditions sufficient to ultimately produce double-stranded DNA for each initial mRNA in the sample that is amplified. During this first step, an RNA polymerase promoter region is incorporated into the resultant product, which region is critical for the second step of the subject methods, i.e. the transcription step described in greater detail infra.

The initial mRNA may be present in a variety of different samples, where the sample will typically be derived from a physiological source. The physiological source may be derived from a variety of eukaryotic sources, with physiological sources of interest including sources derived from single-celled organisms such as yeast and multicellular organisms, including plants and animals, particularly mammals, where the physiological sources from multicellular organisms may be derived from particular organs or tissues of the multicellular organism, or from isolated cells derived therefrom. In obtaining the sample of RNA to be analyzed from the physiological source from which it is derived, the physiological source may be subjected to a number of different processing steps, where such processing steps might include tissue homogenization, cell isolation and cytoplasm extraction, nucleic acid extraction and the like, where such processing steps are known to those of skill in the art. Methods of isolating RNA from cells, tissues, organs or whole organisms are known to those of skill in the art and are described in Maniatis et al. (1989), Molecular Cloning: A Laboratory Manual 2d Ed. (Cold Spring Harbor Press). Alternatively, at least some of the initial steps of the subject methods may be performed in situ, as described in U.S. Pat. No. 5,514,545, the disclosure of which is herein incorporated by reference.

Depending on the nature of the primer employed during first strand synthesis, as described in greater detail below, the subject methods can be used to produce amplified amounts of antisense RNA corresponding to substantially all of the mRNA present in the initial sample, or to a proportion or fraction of the total number of distinct mRNAs present in the initial sample. By substantially all of the mRNA present in the sample is meant more than 90%, usually more than 95%, where that portion not amplified is solely the result of inefficiencies of the reaction and not intentionally excluded from amplification.

The promoter-primer employed in the amplification reaction includes: (a) a poly-dT region for hybridization to the poly-A tail of the mRNA; and (b) an RNA polymerase promoter region 5' of the -poly-dT region that is in an orientation capable of directing transcription of antisense RNA. In certain embodiments, the primer will be a "lock-dock" primer, in which immediately 3' of the poly-dT region is either a "G", "C", or "A" such that the primer has the configuration of 3'-XTTTTTTTT . . . 5', where X is "G", "C", or "A". The poly-dT region is sufficiently long to provide for efficient hybridization to the poly-A tail, where the region typically ranges in length from 10-50 nucleotides in length, usually 10-25 nucleotides in length, and more usually from 14 to 20 nucleotides in length.

A number of RNA polymerase promoters may be used for the promoter region of the first strand cDNA primer, i.e. the promoter-primer. Suitable promoter regions will be capable of initiating transcription from an operationally linked DNA sequence in the presence of ribonucleotides and an RNA polymerase under suitable conditions. The promoter will be linked in an orientation to permit transcription of antisense RNA. A linker oligonucleotide between the promoter and the DNA may be present, and if, present, will typically comprise between about 5 and 20 bases, but may be smaller or larger as desired. The promoter region will usually comprise between about 15 and 250 nucleotides, preferably between about 17 and 60 nucleotides, from a naturally occurring RNA polymerase promoter or a consensus promoter region, as described in Alberts et al. (1989) in Molecular Biology of the Cell, 2d Ed. (Garland Publishing, Inc.). In general, prokaryotic promoters are preferred over eukaryotic promoters, and phage or virus promoters most preferred. As used herein, the term "operably linked" refers to a functional linkage between the affecting sequence (typically a promoter) and the controlled sequence (the mRNA binding site). The promoter regions that find use are regions where RNA polymerase binds tightly to the DNA and contain the start site and signal for RNA synthesis to begin. A wide variety of promoters are known and many are very well characterized. Representation promoter regions of particular interest include T7, T3 and SP6 as described in Chamberlin and Ryan, The Enzymes (ed. P. Boyer, Academic Press, New York) (1982) pp 87-108.

Where one wishes to amplify only a portion of the mRNA species in the sample, one may optionally provide for a short arbitrary sequence 3' of the poly-dT region, where the short arbitrary sequence will generally be less than 5 nucleotides in length and usually less than 2 nucleotides in length, where the dNTP immediately adjacent to the poly-dT region will not be a T residue and usually the sequence will comprise no T residue. Such short 3' arbitrary sequences are described in Ling and Pardee (1992), Science 257, 967.

The promoter-primer described above and throughout this specification may be prepared using any suitable method, such as, for example, the known phosphotriester and phosphite triester methods, or automated embodiments thereof. In one such automated embodiment, dialkyl phosphoramidites are used as starting materials and may be synthesized as described by Beaucage et al. (1981), Tetrahedron Letters 22, 1859. One method for synthesizing oligonucleotides on a modified solid support is described in U.S. Pat. No. 4,458, 066. It is also possible to use a primer that has been isolated from a biological source (such as a restriction endonuclease digest). The primers herein are selected to be "substantially" complementary to each specific sequence to be amplified, i.e.; the primers should be sufficiently complementary to hybridize to their respective targets. Therefore, the primer sequence need not reflect the exact sequence of the target, and can, in fact be "degenerate." Non-complementary bases or longer sequences can be interspersed into the primer, provided that the primer sequence has sufficient complementarity with the sequence of the target to be amplified to permit hybridization and extension.

In the first step of the subject method, the oligonucleotide promoter-primer is hybridized with an initial mRNA sample and the primer-mRNA hybrid is converted to a double-stranded cDNA product that is recognized by an RNA polymerase. The promoter-primer is contacted with the mRNA under conditions that allow the poly-dT site to hybridize to the poly-A tail present on most mRNA species. The catalytic activities required to convert primer-mRNA hybrid to double-stranded cDNA are an RNA-dependent DNA polymerase activity, a RNaseH activity, and a DNA-dependent DNA polymerase activity. Most reverse transcriptases, including those derived from Moloney murine leukemia virus (MMLV-RT), avian myeloblastosis virus (AMV-RT), bovine leukemia virus (BLV-RT), Rous sarcoma virus (RSV) and human immunodeficiency virus (HIV-RT) catalyze each of these activities. These reverse transcriptases are sufficient to convert primer-mRNA hybrid to double-stranded DNA in the presence of additional reagents which include, but are not limited to: dNTPs; monovalent and divalent cations, e.g. KCl, $MgCl_2$; sulfhydryl reagents, e.g. dithiothreitol; and buffering agents, e.g. Tris-Cl. Alternatively, a variety of proteins that catalyze one or two of these activities can be added to the cDNA synthesis reaction. For example, MMLV reverse transcriptase lacking RNaseH activity (described in U.S. Pat. No. 5,405,776) which catalyzes RNA-dependent DNA polymerase activity and DNA-dependent DNA polymerase activity, can be added with a source of RNaseH activity, such as the RNaseH purified from cellular sources, including *Escherichia coli*. These proteins may be added together during a single reaction step, or added sequentially during two or more substeps. Finally, additional proteins that may enhance the yield of double-stranded DNA products may also be added to the cDNA synthesis reaction. These proteins include a variety of DNA polymerases (such as those derived from *E. coli*, thermophilic bacteria, archaebacteria, phage, yeasts, Neurosporas, Drosophilas, primates and rodents), and DNA Ligases (such as those derived from phage or cellular sources, including T4 DNA Ligase and *E. coli* DNA Ligase).

Conversion of primer-mRNA hybrid to double-stranded cDNA by reverse transcriptase proceeds through an RNA: DNA intermediate which is formed by extension of the hybridized promoter-primer by the RNA-dependent DNA polymerase activity of reverse transcriptase. The RNaseH activity of the reverse transcriptase then hydrolyzes at least a portion of the RNA:DNA hybrid, leaving behind RNA fragments that can serve as primers for second strand synthesis (Meyers et al., Proc. Nat'l Acad. Sci. USA (1980) 77:1316 and Olsen & Watson, Biochem. Biophys. Res. Comm. (1980) 97:1376). Extension of these primers by the DNA-dependent DNA polymerase activity of reverse transcriptase results in the synthesis of double-stranded cDNA. Other mechanisms for priming of second strand synthesis may also occur, including "self-priming" by a hairpin loop formed at the 3' terminus of the first strand cDNA (Efstratiadis et al. (1976), Cell 7, 279; Higuchi et al. (1976), Proc. Natl, Acad, Sci USA 73, 3146; Maniatis et al. (1976), Cell 8, 163; and Rougeon and Mach (1976), Proc. Natl. Acad. Sci. USA 73, 3418; and "non-specific priming" by other DNA molecules in the reaction, i.e. the promoter-primer.

The second strand cDNA synthesis results in the creation of a double-stranded promoter region. The second strand cDNA includes not only a sequence of nucleotide residues that comprise a DNA copy of the mRNA template, but also additional sequences at its 3' end which are complementary to the promoter-primer used to prime first strand cDNA synthesis. The double-stranded promoter region serves as a recognition site and transcription initiation site for RNA polymerase, which uses the second strand cDNA as a template for multiple rounds of RNA synthesis during the next stage of the subject methods.

Depending on the particular protocol, the same or different DNA polymerases may be employed during the cDNA synthesis step. In a preferred embodiment, a single reverse transcriptase, most preferably MMLV-RT, is used as a source of all the requisite activities necessary to convert primer-mRNA hybrid to double-stranded cDNA. In another preferred embodiment, the polymerase employed in first strand cDNA synthesis is different from that which is employed in second strand cDNA synthesis. Specifically, a reverse transcriptase lacking RNaseH activity (e.g. Superscript II™) is combined with the primer-mRNA hybrid during a first substep for first strand synthesis. A source of RNaseH activity, such as *E. coli* RNaseH or MMLV-RT, but most preferably MMLV-RT, is added during a second substep to initiate second strand synthesis. In yet other embodiments, the requisite activities are provided by a plurality of distinct enzymes. The manner is which double-stranded cDNA is produced from the initial mRNA is not critical to certain embodiments of the invention. However, the preferred embodiments use MMLV-RT, or a combination of Superscript II™ and MMLV-RT, or a combination of Superscript II™ and *E. coli* RNaseH, for cDNA synthesis as these embodiments yield certain desired results. Specifically, in the preferred embodiments, reaction conditions were chosen so that enzymes present during the cDNA synthesis do not adversely affect the subsequent transcription reaction. Potential inhibitors include, but are not limited to, RNase contaminants of certain enzyme preparations.

The next step of the subject method is the preparation of antisense RNA from the double-stranded cDNA prepared in the first step. During this step, the double-stranded cDNA produced in the first step is transcribed by RNA polymerase to yield antisense RNA, which is complementary to the initial mRNA target from which it is amplified. A critical feature of the invention is that this second step is carried out in the presence of reverse transcriptase which is present in the reaction mixture from the first step. Thus, the subject methods do not involve a step in which the double-stranded cDNA is physically separated from the reverse transcriptase following double-stranded cDNA preparation. Critical to the subject methods is that the reverse transcriptase that is present during the transcription step is rendered inactive. Thus, the transcription step is carried out in the presence of a reverse transcriptase that is unable to catalyze RNA-dependent DNA polymerase activity, at least for the duration of the transcription step. As a result, the antisense RNA products of the transcription reaction cannot serve as substrates for additional rounds of amplification, and the amplification process cannot proceed exponentially.

The reverse transcriptase present during the transcription step may be rendered inactive using any convenient protocol. The transcriptase may be irreversibly or reversibly rendered inactive. Where the transcriptase is reversibly rendered inactive, the transcriptase is physically or chemically altered so as to no longer able to catalyze RNA-dependent DNA polymerase activity. The transcriptase may be irreversibly inactivated by any convenient means. Thus, the reverse transcriptase may be heat inactivated, in which the reaction mixture is subjected to heating to a temperature sufficient to inactivate the reverse transcriptase prior to commencement of the transcription step. In these embodiments, the temperature of the reaction mixture and therefore the reverse transcriptase present therein is typically raised to 55° C. to 70° C. for 5 to 60 minutes, usually to about 65° C. for 15 to 20 minutes. Alternatively, reverse transcriptase may irreversibly inactivated by introducing a reagent into the reaction mixture that chemically alters the protein so that it no longer has RNA-dependent DNA polymerase activity. In yet other embodiments, the reverse transcriptase is reversibly inactivated. In these embodiments, the transcription may be carried out in the presence of an inhibitor of RNA-dependent DNA polymerase activity. Any convenient reverse transcriptase inhibitor may be employed which is capable of inhibiting RNA-dependent DNA polymerase activity a sufficient amount to provide for linear amplification. However, these inhibitors should not adversely affect RNA polymerase activity. Reverse transcriptase inhibitors of interest include ddNTPs, such as ddATP, ddCTP, ddGTP or ddTTP, or a combination thereof, the total concentration of the inhibitor typically ranges from about 50 µM to 200 µM.

For this transcription step, the presence of the RNA polymerase promoter region on the double-stranded cDNA is exploited for the production of antisense RNA. To synthesize the antisense RNA, the double-stranded DNA is contacted with the appropriate RNA polymerase in the presence of the four ribonucleotides, under conditions sufficient for RNA transcription to occur, where the particular polymerase employed will be chosen based on the promoter region present in the double-stranded DNA, e.g. T7 RNA polymerase, T3 or SP6 RNA polymerases, *E. coli* RNA polymerase, and the like. Suitable conditions for RNA transcription using RNA polymerases are known in the art, see e.g. Milligan and Uhlenbeck (1989), Methods in Enzymol. 180, 51. As mentioned above, a critical feature of the subject methods is that this transcription step is carried out in the presence of a reverse transcriptase that has been rendered inactive, e.g. by heat inactivation or by the presence of an inhibitor.

Because of the nature of the subject methods, all of the necessary polymerization reactions, i.e., first strand cDNA synthesis, second strand cDNA synthesis and antisense RNA transcription, may be carried out in the same reaction vessel at the same temperature, such that temperature cycling is not required. As such, the subject methods are particularly suited for automation, as the requisite reagents for each of the above steps need merely be added to the reaction mixture in the reaction vessel, without any complicated separation steps being performed, such as phenol/chloroform extraction. A further feature of the subject invention is that, despite its simplicity, it yields high amplification extents, where the amplification extents (mass of RNA product/mass of RNA target) typically are at least about 50-fold, usually at least about 200-fold and may be as high as 600-fold or higher. Furthermore, such amplification extents are achieved with low variability, e.g. coefficients of variation about the mean amplification extents that do not exceed about 10%, and usually do not exceed about 5%.

The resultant antisense RNA produced by the subject methods finds use in a variety of applications. For example, the resultant antisense RNA can be used in expression profiling analysis on such platforms as DNA microarrays, for construction of "driver" for subtractive hybridization assays, for cDNA library construction, and the like. Especially facilitated by the subject methods are studies of differential gene expression in mammalian cells or cell populations. The cells may be from blood (e.g., white cells, such as T or B cells) or from tissue derived from solid organs, such as brain, spleen, bone, heart, vascular, lung, kidney, liver, pituitary, endocrine glands, lymph node, dispersed primary cells, tumor cells, or the like. The RNA amplification technology can also be applied to improve methods of detecting and isolating nucleic acid sequences that vary in abundance among different populations using the technique known as subtractive hybridization. In such assays, two nucleic acid populations, one sense and the other antisense, are allowed to mix with one another with one population being present in molar excess ("driver"). Under appropriate conditions, the sequences represented in both populations form hybrids, whereas sequences present in only one population remains single-stranded. Thereafter, various well known techniques are used to separate the unhybridized molecules representing differentially expressed sequences. The amplification technology described herein may be used to construct large amounts of antisense RNA for use as "driver" in such experiments.

Depending on the particular intended use of the subject antisense RNA, the antisense RNA may be labeled. One way of labeling which may find use in the subject invention is isotopic labeling, in which one or more of the nucleotides is labeled with a radioactive label, such as $^{32}$S, $^{32}$P, $^{3}$H, or the like. Another means of labeling is fluorescent labeling in which fluorescently tagged nucleotides, e.g. CTP, are incorporated into the antisense RNA product during the transcription step. Fluorescent moieties which may be used to tag nucleotides for producing labeled antisense RNA include: fluorescein, the cyanine dyes, such as Cy3, Cy5, Alexa 542, Bodipy 630/650, and the like. Other labels may also be employed as are known in the art.

Also provided are kits for use in the subject invention, where such kits may comprise containers, each with one or more of the various reagents (typically in concentrated form) utilized in the methods, including, for example, buffers, the appropriate nucleotide triphosphates (e.g. dATP, dCTP, dGTP, dTTP, ATP, CTP, GTP and UTP), reverse transcriptase, RNA polymerase, and the promoter-primer of the present invention. Also present in kits according to the subject invention is a reverse transcriptase inhibitor, where in many embodiments, the inhibitor is at least one ddNTP or a combination of ddNTPs, e.g. ddATP and/or ddGTP. A set of instructions for use of kit components in an mRNA amplification method of the present invention, will also be typically included, where the instructions may be associated with a package insert and/or the packaging of the kit or the components thereof.

The following examples are offered by way of illustration and not by way of limitation.

EXPERIMENTAL

I. Materials and Methods

Example 1

A. Reagents cDNA Synthesis Reaction
1. Poly-A RNA. Human HeLa cell poly-A RNA can be purchased from Clontech, P/N 6522-1

(SEQ ID NO: 01)
DNA T7T18VN (20 µM):
(5') AAT TAA TAC GAC TCA CTA TAG GGA GAT TTT TTT
TTT TTT TTT TTV N (3')
(V = A/C/G, N = A/C/G/T)

3. MMLV Reverse Transcriptase (50 U/µl), Epicentre P/N M4425H
4. RNAGuard, Pharmacia P/N 27-0815-01
5. 5× First Strand Buffer: 250 mM Tris-HCl, pH 8.3, 15 mM MgCl$_2$, 375 mM KCl, Life Technologies P/N 18057-018
6. 100 mM DTT, supplied with MMLV Reverse Transcriptase, Epicentre
7. dNTPs (10 mM each), diluted from Pharmacia P/N 2702035-01
8. Nuclease-free water, Amresco P/N E476

Transcription Reaction
1. T7 RNA Polymerase, Epicentre P/N TU950K
2. RNAGuard, Pharmacia P/N 27-0815-01
3. Inorganic Pyrophosphatase (200 U/ml), diluted from Sigma P/N 1-1891
4. 5× Transcription Buffer: 0.2 M Tris-HCl, pH 7.5, 50 mM NaCl, 30 mM MgCl$_2$, 10 mM spermidine, Epicentre P/N BP001
5. 100 mM DTT, Epicentre P/N BP001
6. MgCl$_2$ (200 mM), diluted from Sigma P/N M-1028
7. NTPs (25 mM ATP, GTP, UTP, 7.5 mM CTP), diluted from Pharmacia P/N 27-2025-01
8. Cy3-CTP OR Cy5-CTP (7.0 mM)
9. Nuclease-free water, Amresco P/N E476
10. Lithium Chloride (4.0 M), diluted from Sigma P/N L-7026
11. 70% ethanol, diluted from Amresco E193
12. TE pH 8.0, Amresco P/N E112

B. Procedure

1. Add 100 ng to 600 ng poly-A RNA to reaction tube. Add 1.0 µl DNA T7T18VN (20 µM) and bring total sample volume to 11.5 µl in nuclease-free water. Incubate 65 C for 10 min to denature primer and template. Quick chill on ice.
2. Mix the following components and maintain on ice. For more than one reaction, multiply by the number of reactions.

| cDNA Mix | |
|---|---|
| Component | Volume (µl) |
| 5× First Strand Buffer | 4.0 |
| 100 mM DTT | 2.0 |
| dNTPs (10 mM each) | 1.0 |
| MMLV-RT (50 U/µl) | 1.0 |
| RNAGuard (36 U/µl) | 0.5 |
| Volume of cDNA Mix | 8.5 |

3. Aliquot 8.5 µl of cDNA Mix into each sample tube.
Incubate cDNA synthesis reaction at 40 C for 120 min.

| Composition of cDNA Synthesis Reaction | |
|---|---|
| Component | Final concentration or amount |
| poly-A RNA | 200 ng |
| DNA T7T18VN | 1 µM |
| Tris-HCl, pH 8.3 | 50 mM |
| MgCl$_2$ | 3.0 mM |
| KCl | 75 mM |
| DTT | 10 mM |
| dNTPs | 0.5 mM each |
| MMLV-RT | 50 U |
| RNAGuard | 18 U |
| Total reaction volume | 20 µl |

4. Incubate reaction tubes at 65 C for 15 min.
Move reaction tubes to ice. Store reactions tubes on ice for 5 min.
5. Immediately before use, mix the following components at room temperature. For more than one reaction, multiply by the number of reactions.

| Transcription Mix | |
|---|---|
| Component | Volume (µl) |
| Nuclease-free water | 20.8 |
| 5× Transcription Buffer | 16 |
| 100 mM DTT | 6.0 |
| NTPs (25 mM A, G, U, 7.5 mM CTP) | 8.0 |
| Cy3-CTP (7.0 mM) OR Cy5-CTP (7.0 mM) | 4.0 |
| 200 mM $MgCl_2$ | 3.3 |
| RNAGuard (36 U/µl) | 0.5 |
| Inorganic Pyrophosphatase (200 U/ml) | 0.6 |
| T7 RNA polymerase (2500 U/µl) | 0.8 |
| Volume of Transcription Mix | 60 |

6. Aliquot 60 µl of Transcription Mix into each sample tube. Incubate transcription reactions at 40 C for 60 min.

| Composition of Transcription Reaction | |
|---|---|
| Component | Final concentration or amount |
| Double-strand cDNA | Approximately 400 ng |
| Tris-HCl, pH 7.5 | 52 mM |
| $MgCl_2$ | 15 mM |
| KCl | 19 mM |
| NaCl | 10 mM |
| Spermidine | 2 mM |
| DTT | 10 mM |
| ATP, GTP, UTP | 2.5 mM each |
| CTP | 0.75 mM |
| Cy3-CTP OR Cy5-CTP | 350 µM |
| T7 RNA polymerase | 2000 U |
| RNAGuard | 18 U |
| Inorganic pyrophosphatase | 0.12 U |
| Total reaction volume | 80 µl |

7. Add 20 µl 50 mM EDTA to each reaction tube to stop the reaction. Alternatively, if quantitation of the amplified RNA product is desired, purify the RNA from unincorporated nucleotides by precipitation of the antisense RNA products in 2.0 M LiCl. Measure the RNA concentration by absorbance at $OD_{260}$ using the conversion: 1 $OD_{260}$=40 µl g/ml RNA. Measure concentration of Cy3-CTP or Cy5-CTP by absorbance at $OD_{552}$ ($\epsilon$=150 (1/mMcm)) or ($\epsilon$=250 (1/mMcm)), respectively.

II. Materials and Methods

Example 2

A. Reagents

First Strand cDNA Synthesis
1. Poly-A RNA. Human HeLa cell poly-A RNA can be purchased from Clontech, P/N 6522-1

```
                                              (SEQ ID NO: 01)
DNA T7T18VN (20 pµ):
(5') AAT TAA TAC GAC TCA CTA TAG GGA GAT TTT TTT
TTT TTT TTT TTV N (3')
(V = A/C/G, N = A/C/G/T)
```

3. Superscript II Reverse Transcriptase, Life Technologies P/N 18064-014
4. RNAGuard, Pharmacia P/N 27-0815-01
5. 5× First Strand Buffer*: 250 mM Tris-HCl, pH 8.3, 15 mM $MgCl_2$, 375 mM KCl
   * supplied with Superscript II Reverse Transcriptase, Life Technologies
6. 100 mM DTT, supplied with Superscript II Reverse Transcriptase, Life Technologies
7. dNTPs (10 mM each), diluted from Pharmacia P/N 2702035-01
8. Nuclease-free water, Amresco P/N E476

Second Strand cDNA Synthesis
1. MMLV Reverse Transcriptase, Epicentre P/N M4425H
2. 5× First Strand Buffer*: 250 mM Tris-HCl, pH 8.3, 15 mM $MgCl_2$, 375 mM KCl, supplied with Superscript II Reverse Transcriptase, Life Technologies
3. dNTPs (10 mM each), diluted from Pharmacia P/N 2702035-01
4. Nuclease-free water, Amresco P/N E476

Transcription Reaction
1. T7 RNA Polymerase, Epicentre P/N TU950K
2. RNAGuard, Pharmacia P/N 27-0815-01
3. Inorganic Pyrophosphatase (200 U/ml), diluted from Sigma P/N I-1898
4. 5× Transcription Buffer: 0.2 M Tris-HCl, pH 7.5, 50 mM NaCl, 30 mM $MgCl_2$, 10 mM spermidine, Epicentre P/N BP001
5. 100 mM DTT, Epicentre P/N BP001
6. $MgCl_2$ (400 mM), diluted from Sigma P/N M-1028
7. NTPs (25 mM ATP, GTP, UTP, 7.5 mM CTP), diluted from Pharmacia P/N 27-2025-01
8. Cy3-CTP OR Cy5-CTP (7.0 mM)
9. ddATP (5 mM), Pharmacia P/N 27-2057-01
10. ddGTP (5 mM), Pharmacia P/N 27-2075-01
11. Nuclease-free water, Amresco P/N E476
12. Lithium Chloride (4.0 M), diluted from Sigma P/N L-7026
13. 70% ethanol, diluted from Amresco E193
14. TE pH 8.0, Amresco P/N E112

B. Procedure

1. Add 100 ng to 600 ng poly-A RNA to reaction tube. Add 1.0 µl DNA T7T18VN (20 µM) and bring total sample volume to 11.5 µl in nuclease-free water. Incubate 70 C for 10 min to denature primer and template. Quick chill on ice.
2. Mix the following components and maintain on ice. For more than one reaction, multiply by the number of reactions.

| Master Mix A | |
|---|---|
| Component | Volume (µl) |
| 5× First Strand Buffer | 4.0 |
| 100 mM DTT | 2.0 |
| dNTPs (10 mM each) | 1.0 |
| Superscript II RT (200 U/µl) | 1.0 |
| RNAGuard (36 U/µl) | 0.5 |
| Volume of Master Mix A | 8.5 |

3. Aliquot 8.5 µl of the master mix A into each sample tube. Incubate first strand synthesis reaction at 40 C for 60 min.

| Composition of First Strand Synthesis Reaction | |
|---|---|
| Component | Final concentration or amount |
| poly-A RNA | 200 ng |
| DNA T7T18VN | 1 µM |
| Tris-HCl, pH 8.3 | 50 mM |

-continued

| Composition of First Strand Synthesis Reaction | |
|---|---|
| Component | Final concentration or amount |
| MgCl$_2$ | 3 mM |
| KCl | 75 mM |
| DTT | 10 mM |
| dNTPs | 0.5 mM each |
| Superscript II RT | 200 U |
| RNAGuard | 18 U |
| Total reaction volume | 20 µl |

4. Mix the following components and maintain on ice. For more than one reaction, multiply by the number of reactions.

| Master Mix B | |
|---|---|
| Component | Volume (µl) |
| 5× First Strand Buffer | 4.0 |
| dNTPs (10 mM each) | 1.0 |
| MMLV-RT (50 U/µl) | 1.0 |
| Nuclease-free water | 13 |
| Volume of master mix B | 20 |

5. Aliquot 20 µl of the Master Mix B into each sample tube. Incubate second strand synthesis reaction at 40 C for 60 min.

| Composition of Second Strand Synthesis Reaction | |
|---|---|
| Component | Final concentration or amount |
| cDNA | Approximately 200 ng |
| Tris-HCl, pH 8.3 | 50 mM |
| MgCl$_2$ | 3 mM |
| KCl | 75 mM |
| DTT | 5 mM |
| dNTPs | 0.5 mM each |
| MMLV-RT | 50 U |
| Total reaction volume | 40 µl |

6. Immediately before use, mix the following components at room temperature. For more than one reaction, multiply by the number of reactions.

| Master Mix C | |
|---|---|
| Component | Volume (µl) |
| Nuclease-free water | 0.8 |
| 5× Transcription Buffer | 16 |
| 100 mM DTT | 6.0 |
| NTPs (25 mM A, G, U, 7.5 mM CTP) | 8.0 |
| Cy3-CTP OR Cy5-CTP (7.0 mM) | 4.0 |
| 400 mM MgCl$_2$ | 1.7 |
| ddATP (5.0 mM) | 0.8 |
| ddGTP (5.0 mM) | 0.8 |
| RNAGuard (36 U/µl) | 0.5 |
| Inorganic Pyrophosphatase (200 U/µl) | 0.6 |
| T7 RNA polymerase (2500 U/µl) | 0.8 |
| Volume of Master Mix C | 40 |

7. Aliquot 40 µl of the master mix C into each sample tube. Incubate transcription reactions at 40 C for 60 min.

| Composition of Transcription Reaction | |
|---|---|
| Component | Final concentration or amount |
| Double-strand cDNA | Approximately 400 ng |
| Tris-HCl, pH 8.1 | 65 mM |
| MgCl$_2$ | 16 mM |
| KCl | 37.5 mM |
| NaCl | 10 mM |
| Spermidine | 2 mM |
| DTT | 10 mM |
| ATP, GTP, UTP | 2.5 mM each |
| CTP | 0.75 mM |
| Cy3-CTP OR Cy5-CTP | 350 µM |
| ddATP, ddGTP | 50 µM each |
| T7 RNA polymerase | 2000 U |
| RNAGuard | 18 U |
| Inorganic pyrophosphatase | 0.12 U |
| Total reaction volume | 80 µl |

8. Add 20 µl 50 mM EDTA to each reaction tube to stop the reaction. Alternatively, if quantitation of the amplified RNA product is desired, purify the RNA from unincorporated nucleotides by precipitation of the antisense RNA products in 2.0 M LiCl. Measure the RNA concentration by absorbance at OD$_{260}$ using the conversion: 1 OD$_{260}$=40 µg/ml RNA. Measure concentration of Cy3-CTP or Cy5-CTP by absorbance at OD$_{552}$ ($\epsilon$=150 (1/mMcm)) or ($\epsilon$=250 (1/mMcm)), respectively.

III. Results

The above protocols provide two variations of the subject method for the amplification of heterogeneous mRNA populations. Both embodiments of the procedure perform essentially equivalently and yield amplification extents (mass of antisense RNA product/mass of mRNA target) up to 600-fold. The products of the amplification reaction are antisense RNA molecules with a size distribution resembling that of the cellular mRNA targets. The antisense RNA products accumulate linearly with respect to time, and thus bias in the relative amounts of specific RNA products associated with exponential amplification is not likely to occur. In fact, the pattern of hybridization intensities on cDNA arrays using fluorescently labeled amplified RNA is very similar to those obtained using labeled cDNA target.

FIG. 1 shows that the amplification method described herein shows significantly higher performance than that described by U.S. Pat. No. 5,716,785. The protocol describing a modification of the method described in this patent that was used for this analysis is found in Appendix A, infra. Amplification extents (micrograms of RNA product/micrograms RNA target) using the amplification method described in this disclosure were significantly higher (average=300) with lower variability (coefficient of variation (CV)=7.0%) than those using the method described by Van Gelder et al. (average=69, CV=35%).

The above results and discussion demonstrate that novel and improved methods of producing linearly amplified amounts of antisense RNA from an initial mRNA source are provided. The subject methods provide for an improvement over prior methods of producing antisense RNA in that the step of separating the double-stranded cDNA from the reverse transcriptase used for its preparation is not required. Instead, all of the steps for linearly amplifying mRNA into antisense RNA may by carried out in a single reaction mixture without performing a separation step. As such, the subject methods are amenable to automation, making them particularly attractive for high throughput applications. Furthermore, linear amplification extents of 600-fold and labeling efficiencies of 8% can be achieved using the subject methods. Finally, all of the benefits of linear amplification are achieved with the subject methods, such as the production of unbiased antisense RNA libraries from heterogeneous mRNA mixtures. As such, the subject methods represent a significant contribution to the art.

All publications and patent application cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

APPENDIX A

Antisense RNA Amplification Using a Modification of the Method Described in Van Gelder et al. U.S. Pat. No. 5,716,785

A. Reagents:
First Strand cDNA Synthesis
1. Poly-A RNA. Human HeLa Cell poly-A RNA can be purchased from Clontech, P/N 6522-1
2. DNA T7T18VN (20 μM): (5') AAT TAA TAC GAC TCA CTA TAG GGA GAT TTT TTT TTT TTT TTT TTV N (3') (V=A/C/G, N=A/C/G/T)
3. Superscript II Reverse Transcriptase, Life Technologies P/N 18064-014
4. RNAGuard, Pharmacia P/N 27-0815-01
5. 5× First Strand Buffer*: 250 mM Tris-HCl, pH 8.3, 15 mM MgCl$_2$, 375 mM KCl
   * supplied with Superscript II Reverse Transcriptase, Life Technologies
6. 100 mM DTT*
   * supplied with Superscript II Reverse Transcriptase, Life Technologies
7. dNTPs (10 mM each), diluted from Pharmacia P/N 2702035-01
8. Nuclease-free water, Amresco P/N E476
Second Strand cDNA Synthesis
12. E. coli DNA polymerase I, Life Technologies P/N 18010-017
12. E. coli RNaseH, Life Technologies P/N 18021-014
12. E. coli DNA Ligase, Life Technologies P/N 18052-019
12. T4 DNA polymerase, Epicentre P/N D0602H
12. 5× Second Strand Buffer: 100 mM Tris-HCl, pH 6.9, 23 mM MgCl$_2$, 450 mM KCl, 0.75 mM β-NAD+, 50 mM (NH$_4$)$_2$SO$_4$, Life Technologies P/N 10812014
12. dNTPs (10 mM each), diluted from Pharmacia P/N 2702035-01
12. Nuclease-free water, Amresco P/N E476
12. EDTA 0.5 M, Amresco P/N E522 (or equivalent)
12. Phenol:chloroform:isoamyl alcohol (25:24:1), Amresco P/N 0883 (or equivalent)
12. Ammonium Acetate 7.5 M, Sigma P/N A2706
12. 100% ethanol, Amresco P/N E193
12. 70% ethanol, diluted from Amresco P/N E193
Transcription Reaction
1. T7 RNA Polymerase, Epicentre P/N TU950K
2. RNAGuard, Pharmacia P/N 27-0815-01
3. Inorganic Pyrophosphatase (200 U/ml)
4. 5× Transcription Buffer: 0.2 M Tris-HCl, pH 7.5, 50 mM NaCl, 30 mM MgCl$_2$, 10 mM spermidine, Epicentre P/N BP001
5. 100 mM DTT, Epicentre P/N BP001
6. MgCl$_2$ (400 mM), diluted from Sigma P/N M-1028
7. NTPs (25 mM each), diluted from Pharmacia P/N 27-2025-01
8. Nuclease-free water, Amresco P/N E476
9. Lithium Chloride (4.0 M), diluted from Sigma P/N L-7026
10. 70% ethanol, diluted from Amresco P/N E193
11. TE pH 8.0, Amresco P/N E112

B. Procedure:
1. Add 100 ng to 600 ng poly-A RNA to reaction tube. Add 1.0 μl DNA T7T18VN (20 μM) and bring total sample volume to 11.5 μl in nuclease-free water. Incubate 70 C for 10 min to denature primer and template. Quick chill on ice.
2. Mix the following components and maintain on ice. For more than one reaction, multiply by the number of reactions.

| Master Mix A | |
|---|---|
| Component | Volume (μl) |
| 5× First Strand Buffer | 4.0 |
| 100 mM DTT | 2.0 |
| dNTPs (10 mM each) | 1.0 |
| Superscript II RT (200 U/μl) | 1.0 |
| RNAGuard (36 U/μl) | 0.5 |
| Volume of Master Mix A | 8.5 |

3. Aliquot 8.5 μl of the master mix A into each sample tube. Incubate first strand synthesis reaction at 37 C for 60 min.

| Composition of First Strand Synthesis Reaction | |
|---|---|
| Component | Final concentration or amount |
| poly-A RNA | 600 ng |
| DNA T7T18VN | 1 μM |
| Tris-HCl, pH 8.3 | 50 mM |
| MgCl$_2$ | 3 mM |
| KCl | 75 mM |
| DTT | 10 mM |
| dNTPs | 0.5 mM each |
| Superscript II RT | 200 U |
| RNAGuard | 18 U |
| Total reaction volume | 20 μl |

4. Mix the following components and maintain on ice. For more than one reaction, multiply by the number of reactions.

Note: If the activities of the enzymes are different than indicated below, add the appropriate volume to give the Units per reaction indicated below.

| Master Mix B | | |
| --- | --- | --- |
| Component | Volume (μl) | Units |
| Nuclease-free water | 91 | |
| 5× Second Strand Buffer | 30 | |
| dNTPs (10 mM each) | 3.0 | |
| E. coli DNA Ligase (10 U/μl) | 1.0 | 10 |
| E. coli DNA polymerase I (10 U/μl) | 4.0 | 40 |
| E. coli RNaseH (2 U/μl) | 1.0 | 2 |
| Volume of master mix B | 130 | |

5. On ice, aliquot 130 μl of the Master Mix B into each sample. Incubate second strand synthesis reaction at 16 C for 120 min.
Note: Second strand synthesis reactions are incubated at 16 C to inhibit strand displacement by DNA polymerase I. Do not let the temperature rise above 16 C.

| Composition of Second Strand Synthesis Reaction | |
| --- | --- |
| Component | Final concentration or amount |
| Single-strand cDNA | Approximately 600 ng |
| Tris-HCl, pH 7.5 | 25 mM |
| $MgCl_2$ | 5 mM |
| KCl | 100 mM |
| β-$NAD^+$ | 0.15 mM |
| 10 mM $(NH_4)_2SO_4$ | 10 mM |
| DTT | 1.2 mM |
| dNTPs | 0.25 mM each |
| E. coli DNA Ligase | 10 U |
| E. coli DNA Polymerase I | 40 U |
| E. coli RNaseH | 2 U |
| Total reaction volume | 150 μl |

6. Add 2 μl T4 DNA polymerase (10 U) to each sample tube. Incubate 16 C for 5 min.
7. Add 10 μl of 0.5 M EDTA to each sample tube.
8. Add 150 μl of phenol:chloroform:isoamyl alcohol (25:24:1). Vortex thoroughly and spin 5 min at room temperature in microcentrifuge. Carefully remove 140 μl of the upper, aqueous phase and transfer to fresh reaction tube.
9. Add 70 μl 7.5 M $NH_4OAc$ and 0.5 ml 100% ethanol to each sample tube. Mix and spin 20 min at 4 C in microcentrifuge. Rinse each sample pellet in 70% ethanol. Dry pellet briefly at room temperature. Resuspend each sample pellet in 40 μl nuclease-free water.
10. Immediately before use, mix the following components at room temperature. For more than one reaction, multiply by the number of reactions.

| Master Mix C | |
| --- | --- |
| Component | Volume (μl) |
| Nuclease-free water | 4.1 |
| 5× Transcription Buffer | 16 |
| 100 mM DTT | 8.0 |
| NTPs (25 mM each) | 8.0 |
| 400 mM $MgCl_2$ | 2.0 |
| RNAGuard (36 U/μl) | 0.5 |
| Inorganic Pyrophosphatase (200 U/μl) | 0.6 |
| T7 RNA polymerase (2500 U/μl) | 0.8 |
| Volume of Master Mix C | 40 |

11. Aliquot 40 μl of the master mix C into each sample tube. Incubate transcription reactions at 37 C for 60 min.

| Composition of Transcription Reaction | |
| --- | --- |
| Component | Final concentration or amount |
| Double-strand cDNA | Approximately 1200 ng |
| Tris-HCl, pH 7.5 | 50 mM |
| $MgCl_2$ | 16 mM |
| NaCl | 10 mM |
| Spermidine | 2 mM |
| DTT | 10 mM |
| NTPs | 2.5 mM each |
| T7 RNA polymerase | 2000 U |
| RNAGuard | 18 U |
| Inorganic pyrophosphatase | 0.12 U |
| Total reaction volume | 80 μl |

12. Add 20 μl 50 mM EDTA to each reaction tube to stop the reaction. Alternatively, if quantitation of the amplified RNA product is desired, purify the RNA from unincorporated nucleotides by precipitation of the antisense RNA products in 2.0 M LiCl. Measure the RNA concentration by absorbance at $OD_{260}$ using the conversion: 1 $OD_{260}$=40 μg/ml RNA.

What is claimed is:

1. A method for producing RNA, comprising:
   (a) converting an RNA molecule to double-stranded cDNA, wherein one terminus of the double-stranded cDNA comprises an RNA polymerase promoter region; and
   (b) transcribing the double-stranded cDNA with an RNA polymerase and ribonucleotides in the presence of a reverse transcriptase that is incapable of RNA-dependent DNA polymerase activity during the transcribing step.

2. The method according to claim 1, wherein the method further comprises inactivating the reverse transcriptase prior to the transcribing step.

3. The method according to claim 2, wherein the inactivation is accomplished by heating the reaction mixture.

4. The method according to claim 1, wherein the method further comprises inhibiting the reverse transcriptase with an inhibitor during the transcribing step.

5. The method according to claim 4, wherein the inhibitor is at least one ddNTP.

6. The method according to claim 1, wherein the converting step comprises a single cDNA synthesis step, wherein the same polymerase is employed for the synthesis of first and second cDNA strands.

7. The method according to claim 1, wherein the converting step comprises a first strand cDNA synthesis step and a second strand cDNA synthesis step.

8. The method according to claim 7, wherein a first polymerase is employed for synthesis of the first strand cDNA, which is lacking RNaseH activity.

9. The method according to claim 1, wherein the converting step employs a promoter-primer comprising an RNA binding site for the RNA molecule linked to a promoter sequence.

10. A method for producing RNA comprising:
    (a) converting an RNA molecule to cDNA with a promoter-primer comprising a binding site for the RNA molecule linked to an RNA polymerase promoter sequence; and
    (b) transcribing the cDNA with an RNA polymerase and ribonucleotides in the presence of a reverse transcriptase that has been rendered ineffective for RNA-dependent DNA polymerase activity prior to the transcribing step.

11. The method according to claim 10, wherein the method further comprises inactivating the reverse transcriptase prior to the transcribing step.

12. The method according to claim 11, wherein the inactivation is accomplished by heating the reaction mixture.

13. The method according to claim 10, wherein the method further comprises inhibiting the reverse transcriptase with an inhibitor during the transcribing step.

14. The method according to claim 13, wherein the inhibitor is at least one ddNTP.

15. A method for producing RNA comprising:
    (a) converting an RNA molecule to double-stranded cDNA by:
        (i) contacting the RNA molecule with a promoter-primer under conditions wherein the RNA molecule forms a complex with the promoter-primer, wherein the promoter-primer comprises a binding site for the RNA molecule linked to a RNA promoter sequence; and
        (ii) converting the complex to double-stranded cDNA using a combination of RNA-dependent DNA polymerase activity, RNaseH activity and DNA-dependent DNA polymerase activity; and
    (b) transcribing the double-stranded cDNA with an RNA polymerase and ribonucleotides in the presence of a reverse transcriptase that is incapable of RNA-dependent DNA polymerase activity during the transcribing step.

16. The method according to claim 15, wherein the RNA-dependent DNA polymerase activity, RNaseH activity and DNA-dependent DNA polymerase activity are contributed by a single polymerase.

17. The method according to claim 16, wherein the polymerase is the reverse transcriptase of Moloney Murine leukemia virus (MMLV-RT).

18. The method according to claim 16, wherein the polymerase is the reverse transcriptase of avian myeloblastosis virus (AMV-RT).

19. The method according to claim 15, wherein the RNA-dependent DNA polymerase activity is inhibited with ddNTPs.

20. A method for producing RNA comprising:
    (a) contacting an RNA molecule with a promoter-primer in the presence of a first reverse transcriptase under conditions sufficient for first strand cDNA synthesis to occur to produce a hybrid of the RNA molecule and a first strand cDNA, wherein the promoter-primer comprises an binding site for the RNA molecule linked to a RNA polymerase promoter sequence;
    (b) contacting the hybrid with an enzyme having RNaseH activity under conditions sufficient to convert the complex to a double-stranded cDNA molecule; and
    (c) transcribing the double-stranded cDNA with an RNA polymerase and ribonucleotides in the presence of ddNTPs and said reverse transcriptase, wherein said reverse transcriptase is incapable of RNA-dependent DNA polymerase activity.

21. The method according to claim 20, wherein the enzyme catalyzing RNaseH activity is the reverse transcriptase of Moloney Murine leukemia virus (MMLV-RT).

22. The method according to claim 20, wherein the enzyme catalyzing RNaseH activity is the RNaseH of *Escherichia coli* (*E. coli* RNaseH).

23. The method according to claim 20, wherein the RNA polymerase promoter is the T7 promoter and the RNA polymerase is T7 RNA polymerase.

24. The method according to claim 20, wherein the RNA polymerase promoter is the T3 promoter and the RNA polymerase is T3 RNA polymerase.

25. The method according to claim 20, wherein the ddNTPs are selected from the group consisting of: ddATP and ddGTP.

26. The method according to claim 1, wherein no more than one thermal cycling reaction occurs.

27. The method according to claim 1, wherein the double-stranded cDNA is not physically separated from the reverse transcriptase following double-stranded cDNA preparation.

28. The method of claim 1 wherein the reverse transcriptase is irreversibly incapable of RNA-dependent DNA polymerase activity during the transcribing step.

* * * * *